United States Patent [19]

Davis

[11] Patent Number: 4,953,819

[45] Date of Patent: Sep. 4, 1990

[54] ADJUSTABLE SUPPORT CLAMP APPARATUS AND METHOD

[76] Inventor: Dale C. Davis, 2531 Bonita St., Lemon Grove, Calif. 92045

[21] Appl. No.: 437,024

[22] Filed: Nov. 15, 1989

[51] Int. Cl.$^5$ ............................................. A47B 96/06
[52] U.S. Cl. ..................................... 248/230; 211/107
[58] Field of Search ............... 248/230, 231, 124, 125, 248/122; 211/107; 24/532, 457, 71 A

[56] References Cited

U.S. PATENT DOCUMENTS

| | | | |
|---|---|---|---|
| 561,664 | 6/1896 | Hollister . | |
| 2,299,837 | 10/1942 | Mayer | 248/231 |
| 2,496,478 | 2/1950 | Kinnebrew | 248/231 UX |
| 2,579,975 | 12/1951 | Scott et al. | 24/71 A |
| 3,318,457 | 5/1967 | Krasnoff | 248/125 X |
| 3,559,941 | 2/1971 | Holzman | 248/231 X |
| 4,030,690 | 6/1977 | Hanauer | 248/125 X |
| 4,144,673 | 3/1979 | Quast | 211/107 X |
| 4,382,570 | 5/1983 | Craig . | |
| 4,383,252 | 5/1983 | Purcell | 248/124 X |
| 4,666,111 | 5/1987 | Schuler | 248/125 |
| 4,706,368 | 11/1987 | Crissman | 248/122 X |

FOREIGN PATENT DOCUMENTS

| | | | |
|---|---|---|---|
| 293151 | 2/1932 | Italy | 24/71 A |
| 11901 | of 1899 | United Kingdom | 211/107 |

Primary Examiner—J. Franklin Foss
Attorney, Agent, or Firm—Andsel Group, Inc.

[57] ABSTRACT

An adjustable support clamp apparatus and method for clamping is defined. The support clamp has two arcuate pliable bands with an adjustable coacting connection at their first adjoining ends and a coacting off-center tension clamp at their second adjoining ends. There is a resilient pliable gasket, with a textured surface, secured to each of the arcuate pliable bands. The adjustable connection at the first adjoining ends has an extension on a first band with a plurality of ports into which are placed a joining means that is on the end of a second extension of the second band. The joining means hinges in the ports to provide easy opening and closing of the clamp around a pole or barlike object and to provide a clamp that will adjust its diameter to accommodate poles or bars with varying diameters. The clamp has a plurality of supporting means that have a shaft with a spiral hook at one end and has its other end pivotally attached to the arcuate pliable bands.

10 Claims, 1 Drawing Sheet

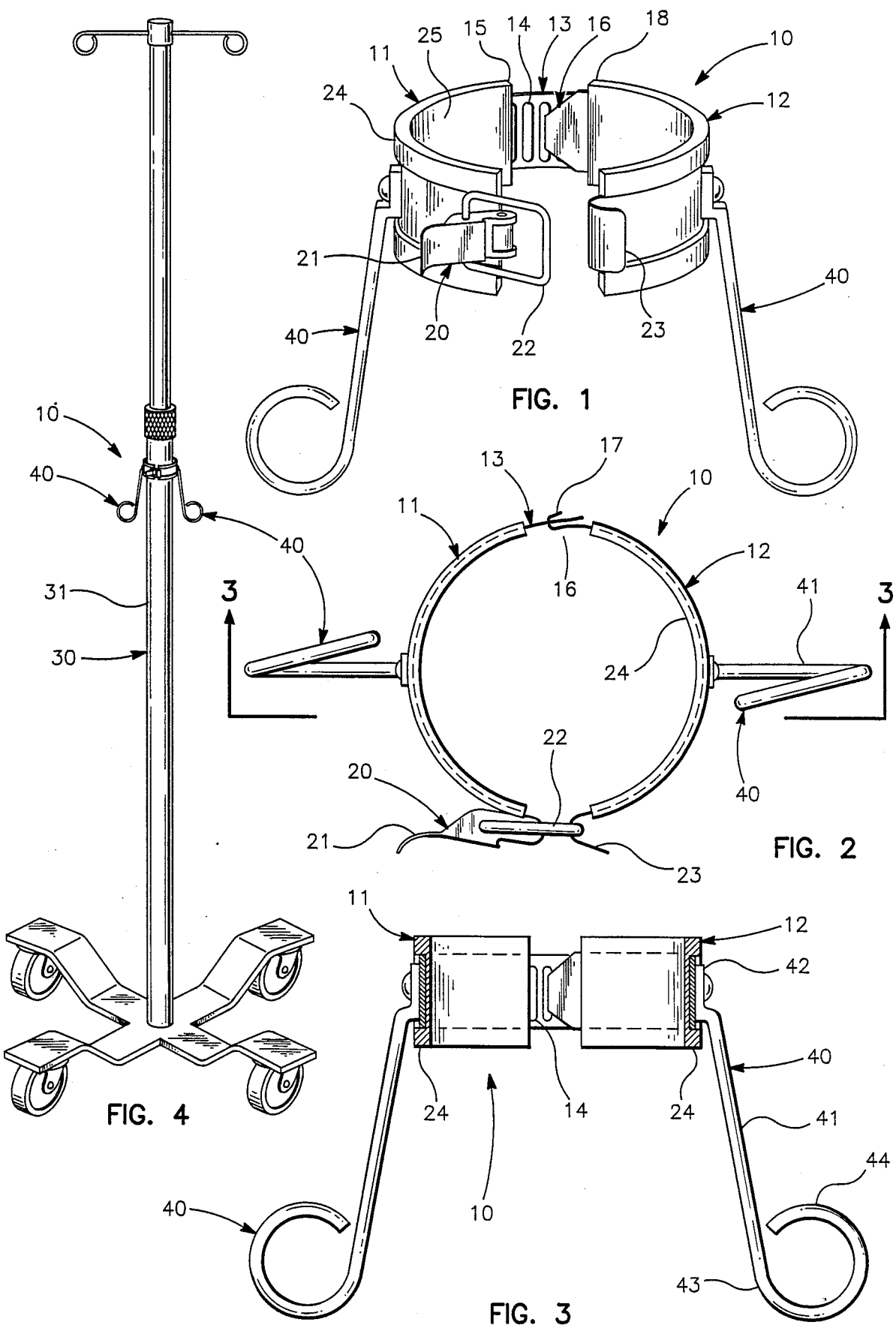

ADJUSTABLE SUPPORT CLAMP APPARATUS AND METHOD

BACKGROUND OF THE INVENTION

1. Field of the Invention

This invention relates to an adjustable support clamp apparatus and method for using it. The clamp apparatus may be clamped securely to a polelike apparatus such as that used by medical facilities and is used to detachably support plasma bottles, IV bags and the like to aid in the treatment of patients. The clamps may be loosened, positioned and resecured at various heights on the pole or to other suitable apparatus to which the clamp may attach. Since the diameter of the supporting pole or other apparatus may vary, the clamp defined herein has an adjustable feature which allows the user to change the diameter of the clamp.

An IV pole is approximately a seven foot telescopingly adjustable pole usually on wheels. The diameter of the telescoping sections vary requiring a clamp that will adapt. Often an overhead bar is used to hang various medical paraphernalia that needs to be placed higher that the pole can extend or to hang material when a pole is unavailable. Therefore there is a need for a clamp that will clamp in many areas quickly and easily.

2. Description of the Related Art

In the past, various configurations of clamps have been used in many ways to solve many problems. Ease of use and adaptability to varying diameters has always presented a problem that various devices have tried to solve.

A Great Britain Patent No. 24964 to Avery in Nov. 1909 shows an early clamp. This clamp was rigid, nonadjustable and did not have pivotable supporting means. The clamp had to be unbolted to transfer it to another pole and had no resilient textured gasket.

A U.S. Pat. No. 4,382,570 to John L. Craig on May 10, 1983 shows a nonadjustable clamp that has three arcuate bands and a two-piece mounting foot.

A U.S. Pat. No. 561,664 to S.T. Hollister on June 9, 1896 shows a multi-sectioned clothes drier with reciprocal fastening devices that form pockets in which may be placed springwire loops. The device is expandable by more sections and has no resilient, textured gasket.

SUMMARY OF THE INVENTION

The present invention is a support clamp with two arcuate pliable bands with an adjustable coacting connection at their first adjoining ends and a coacting off-center tension clamp at their second ends. There is a resilient pliable gasket secured to each of the two arcuate pliable bands. The gasket has a textured surface. There is a plurality of supporting means attached to the arcuate pliable bands to support items.

The adjustably coacting connection may have a first flexible extension with a plurality of ports on a third end of a first band of the two bands and a second flexible connection with a joining means on a fourth end of a second band of the two bands to enter the ports and hingingly join the two bands.

The supporting means may have a shaft with a spiral hook on one end.

The supporting means may have a spiral hook on a fifth end of the shaft and have a sixth end of the shaft attached to the arcuate pliable bands to Support items.

The sixth end of the shaft may be pivotally attached to the arcuate pliable bands.

A method for clamping by providing two arcuate pliable bands and connecting their adjoining ends with an adjustably coacting connection and clamping their second adjoining ends with a coacting off-center tension clamp. The method includes securing a resilient pliable gasket to each of the arcuate pliable bands and placing a texture on the surface of the gasket. Also included in the method is attaching a plurality of supporting means to the arcuate pliable bands to support items.

The method may include, in connecting their first adjoining ends, providing a first flexible extension with a plurality of ports on a third end of a first band of the two bands and hingingly joining the two bands by providing a second flexible extension with a joining means on a fourth end of a second band of the two bands to enter and hinge in the ports.

The method may include, in the attaching a plurality of supporting means, using a shaft with a spiral hook at one end of the shaft. the method may also include providing a plurality of supporting means having a spiral hook at a fifth end of a shaft and having a sixth end of the shaft pivotally attached to the arcuate pliable bands to support items.

It is therefore one object of this invention to provide a support clamp whose diameter is adjustable in order that the clamp may be attached to rodlike devices such as poles or overhead bars whose diameters may vary in size without the inconvenience of obtaining and securing another clamp or securing multiple clamps.

It is an object of this invention to provide a support clamp that is easily attached and released by way of a coacting off-center tension clamp.

It is another object of this invention to provide a support clamp that has a resilient pliable gasket with a textured surface that will aid in securely clamping the clamp to the pole or rod by compressing slightly and by having the textured surface grip the pole surface to reduce the chance of slippage of the clamp.

It is yet another object of this invention to provide a support clamp with a plurality of supporting means that have a pivotable shaft attached to the bands and a spiral hook at one end to detachably support items placed on them.

It is an object of this invention to provide a method for clamping.

BRIEF DESCRIPTION OF THE DRAWINGS

FIG. 1 is a perspective view showing the support clamp in an open configuration.

FIG. 2 is a bottom view of the support clamp in a closed configuration.

FIG. 3 is a cross-sectional view of the support clamp taken along line 3—3 of FIG. 2.

FIG. 4 is a perspective view of the support clamp placed on a typical IV pole.

DESCRIPTION OF THE PREFERRED EMBODIMENT

Referring to FIGS. 1, 2 and 3, the support clamp 10 has two arcuate pliable bands, a first band 11 and a second band 12. A first flexible extension 13 with a plurality of ports 14 is attached to or made part of a third end 15 of the first band 11. There is a second flexible extension 16 with a joining means 17 on a fourth end 18 of a second band 12. The joining means is placed into one of the ports 14 allowing the two bands to hinge at the connection of the port 14 and joining means 17. Joining means 17 could be a curved tapered end as shown in FIGS. 1, 2 and 3. The coacting off-center tension clamp 20 consists of three basic parts: a clasp 21, a loop 22 and a hook 23. The loop 22 is positioned on the hook 23 and the clasp 21 is pressed to the closed position securing the support clamp to, for example, the pole 30 or to a rod (not shown).

There is a resilient pliable gasket 24 secured to both band 11 and band 12. The gasket 24 has a textured surface 25 that reduces the occurrence of slippage of the support clamp when the support clamp is secured on a smooth surface 31 found on IV pole 30 (FIG.4) or other like surfaces.

There are a plurality of supporting means 40 that have a shaft 41 with a fifth end 42 pivotally attached to arcuate pliable band 11 and to arcuate pliable band 12. On the sixth end 43 of the shaft 41 is a spiral hook 44. The supporting means 40 allow the user to detachably support items such as IV bags or plasma bottles as required by the user. The shape of the spiral hooks allow for easy attaching and removal of the items and reduce the possibility of the items becoming dislodged accidentally.

The arcuate pliable bands and the flexible extensions may be made of metal such as stainless steel, a plastic, or other suitable material. The resilient pliable gasket may be made of a rubber, elastic rubberlike material or suitable pliable plastic material or the like.

The foregoing descriptions and drawings of the invention are explanatory and illustrative only, and various changes in shapes, sizes and arrangement of parts as well as certain details of the illustrated construction may be made within the scope of the appended claims without departing from the true spirit of the invention.

I claim:

1. A support clamp comprising:
   a. two arcuate pliable bands;
   b. an adjustably coacting connection at their first adjoining ends;
   c. a coacting off-center tension clamp at their second adJoining ends;
   d. a resilient pliable gasket secured to each of the two arcuate pliable bands;
   e. a textured surface on the gasket; and
   f. a plurality of supporting means attached to the arcuate pliable bands to support items.

2. A support clamp as defined in claim 1 wherein the adjustably coacting connection comprises:
   a. a first flexible extension with a plurality of ports on a third end of a first band of the two bands; and
   b. a second flexible extension with a joining means on a fourth end of a second band of the two bands to enter the ports and hingingly join the two bands.

3. A support clamp as defined in claim 1 wherein the supporting means comprises a shaft with a spiral hook on one end of the shaft.

4. A support clamp comprising:
   a. two arcuate pliable bands;
   b. a first flexible extension with a plurality of ports on a third end of a first band of the two bands;
   c. a second flexible extension with a joining means on a fourth end of a second band of the two bands to enter the ports and hingingly join the two bands at their first adjoining ends;
   d. a coacting off-center tension clamp at their second adjoining ends;
   e. a resilient pliable gasket secured to each of the two arcuate pliable bands;
   f. a textured surface on the gasket; and
   g. a plurality of supporting means having a shaft with a spiral hook at a fifth end of the shaft and having a sixth end of the shaft attached to the arcuate pliable bands to support items.

5. A support clamp as defined in claim 4 wherein the sixth end of the supporting means is pivotally attached to the arcuate pliable bands.

6. A support clamp comprising:
   a. two arcuate pliable bands;
   b. a first flexible extension with a plurality of ports on a third end of a first band of the two bands;
   c. a second flexible extension with a joining means on a fourth end of a second band of the two bands to enter the ports and hingingly join the two bands at their first adjoining ends;
   d. a coacting off-center tension clamp at their second adjoining ends;
   e. a resilient pliable gasket secured to each of the two arcuate pliable bands;
   f. a textured surface on the gasket; and
   g. a plurality of supporting means having a shaft with a spiral hook at a fifth end of the shaft and having a sixth end of the shaft pivotally attached to the arcuate pliable bands to support items.

7. A method for clamping comprising
   a. providing two arcuate pliable bands;
   b. connecting their first adjoining ends with an adjustably coacting connection;
   c. clamping their second adjoining ends with a coacting off-center tension clamp;
   d. securing a resilient pliable gasket to each of the arcuate pliable bands;
   e. placing a texture on the surface of the gasket; and
   f. attaching a plurality of supporting means to the arcuate pliable bands to support items.

8. A method for clamping as defined in claim 7 wherein connecting their first adjoining ends further comprises:
   a. providing a first flexible extension with a plurality of ports on a third end of a first band of the two bands; and
   b. hingingly joining the two bands by providing a second flexible extension with a joining means on a fourth end of a second band of the two bands to enter and hinge in the ports.

9. A method for clamping items as defined in claim 7 wherein attaching a plurality of supporting means further comprises using a shaft with a spiral hook on one end of the shaft.

10. A method for clamping comprising:
    a. providing two arcuate pliable bands;
    b. providing a first flexible extension with a plurality of ports on a third end of a first band of the two bands;
    c. hingingly joining the two bands by providing a second flexible extension with a joining means on a fourth end of a second band of the two bands to enter and hinge in the ports;
    d. clamping the second adjoining ends of the two bands with a coacting off-center tension clamp;
    e. securing a resilient pliable gasket to each of the arcuate pliable bands;
    f. placing a texture on the surface of the gasket; and
    g. providing a plurality of supporting means having a spiral hook at a fifth end of a shaft and having a sixth end of the shaft pivotally attached to the arcuate pliable bands to support items.

* * * * *